United States Patent

Brunken

[11] Patent Number: 5,683,415
[45] Date of Patent: Nov. 4, 1997

[54] SURGICAL NEEDLE

[75] Inventor: Dieter Brunken, Huttblek, Germany

[73] Assignee: Ethicon, Inc., Somerville, N.J.

[21] Appl. No.: 441,844

[22] Filed: May 16, 1995

Related U.S. Application Data

[63] Continuation of Ser. No. 299,461, Aug. 29, 1994, abandoned.

[30] Foreign Application Priority Data

Mar. 13, 1992 [DE] Germany .................. 42 08 242.0

[51] Int. Cl.⁶ .................................................. A61B 17/06
[52] U.S. Cl. ........................................ 606/222; 148/242
[58] Field of Search ............................ 606/222; 148/242

[56] References Cited

U.S. PATENT DOCUMENTS 3,840,015  10/1974  Gain ............................... 606/222
4,905,695   3/1990  Bendel et al. ................ 606/222
4,959,068   9/1990  Bendel et al. ................ 606/222

*Primary Examiner*—Michael Buiz
*Assistant Examiner*—Kevin Truong
*Attorney, Agent, or Firm*—Emil Richard Skula

[57] ABSTRACT

The invention relates to a surgical needle with a suture material or thread fixed to the end opposite to the perforation tip, characterized in that the puncturing tip and the area of the needle following onto the latter is made up to approximately 50% of its length from bare or surface-untreated metal, whereas the surface of the remaining part of the needle and up to the thread shoulder is chemically or electrolytically of a coating dulled or coloured in a continuous manner or with minor interruptions.

10 Claims, 3 Drawing Sheets

SURGICAL NEEDLE

This is a continuation of application Ser. No. 08/299,461, filed Aug. 29, 1994 now abandoned.

FIELD OF THE INVENTION

The invention relates to a surgical needle with a suture material or thread fixed to the end opposite to the puncturing tip.

BACKGROUND OF THE INVENTION

Such surgical needles or suture needles are generally known and are normally made from a corrosion-resistant metal, preferably chrome-nickel steel. Bare or surface-untreated needles are used for minor surgical operations. However, in the case of major surgery, of late so-called coloured or dulled needles have been used, such as are e.g. described in U.S. Pat. No. 4,959,068. This colouring or dulling takes place either chemically by pickling or etching or electrolytically by a corresponding anodic or cathodic treatment, optionally with polarity reversal or by alternating current. A special form of pickling is so-called dull pickling. In certain cases stoving lacquers are also used for colouring or dulling. As a result of the so-called colouring or dulling of the surgical needle, the latter does not reflect under powerful OP-light and irritate the surgeon, which is particularly advantageous in major operations.

Despite the popularity of such coloured or dulled needles, it has proved disadvantageous that particularly with yellow to dark red and brown coloured or dulled needles the surgeon is unable to precisely detect in the similarly coloured tissue or operating field the point of perforation of the needle, i.e. the needle tip and the area following onto the same, which makes it more difficult to precisely insert a suture not only in microsurgery, but in general surgical operations.

SUMMARY OF THE INVENTION

The problem of the invention is to eliminate this disadvantage and make available a surgical needle, which has both the advantage of coloured or dulled needles, i.e. freedom from glare, whilst simultaneously permitting a precise point-sized insertion of the needle into the corresponding tissue.

Thus, for solving the set problem, a surgical needle of the aforementioned construction is proposed, which is constructed in such a way that the puncturing tip and the area of the needle following onto the latter is made up to approximately 50% of its length from bare or surface-untreated metal, whereas the surface of the remaining part of the needle and up to the thread shoulder is chemically or electrolytically or by means of a coating dulled or coloured in a continuous manner or with minor interruptions.

It has surprisingly been found that with a needle according to the invention in this form and contrary to the previously held opinion that the entire needle must be dulled or coloured, it is still possible to operate in a glare-free manner and that with the relatively short tip of the bare or surface-untreated metal it is possible to insert a suture much more accurately.

Preferably the bare or surface-untreated area represents less than 25% of the needle length, said value also being dependent on the needle size or length and in absolute terms can in particular be 4 to 10 mm.

In place of a continuous dulling or colouring of the remaining part of the needle, the latter can be dulled or coloured with minor interruptions and in particular this coloured or dulled area can be dulled or coloured in ring form or in speckled form. The bare gaps in the only zonally dulled or coloured area are preferably no larger than 1 to 2 mm.

The invention is described in greater detail hereinafter relative to the drawings, wherein show:

DETAILED DESCRIPTION OF THE EMBODIMENTS

Figure 1:
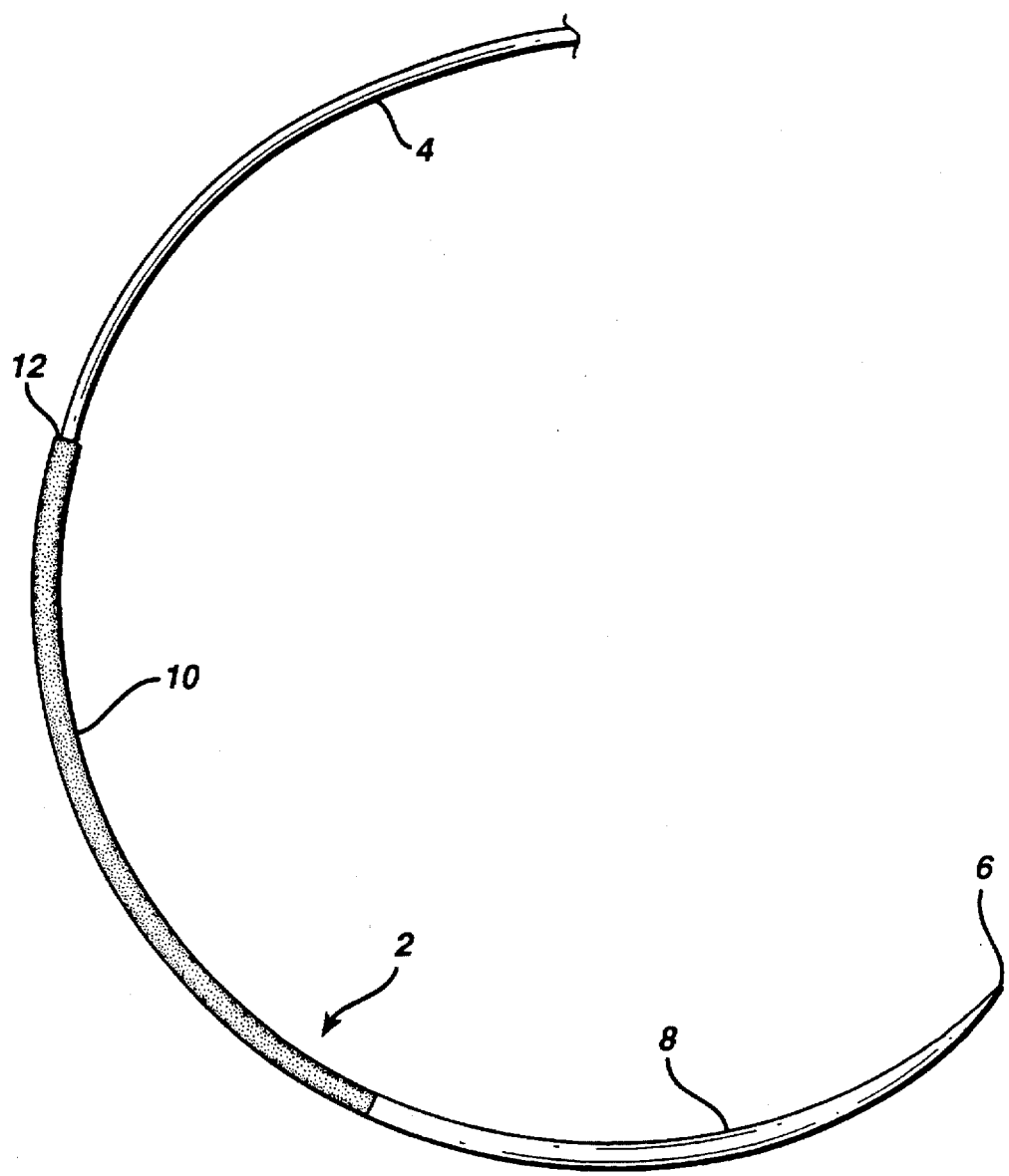
FIG. 1 a larger-scale representation of the surgical needle according to the invention with a continuously dulled or coloured area.

The needle 2 is a standard semicircular round body needle. However, the needle can have any other random configuration and can e.g. be a blunt round body needle, a cutting needle or a spatula needle. At one end of the needle is located the perforation or puncturing tip 6, which can also be constructed as a microtip, whereas at the opposite end of the needle it is possible to see the thread shoulder 12 with the thread 4. The tip 6 and the area 8 following onto it and which represents approximately less than 50% of the needle length, is bare or surface-untreated, whereas the remaining part 10 is continuously dulled or coloured either chemically or electrolytically on the one hand, or by means of a coating on the other.

Figure 2:
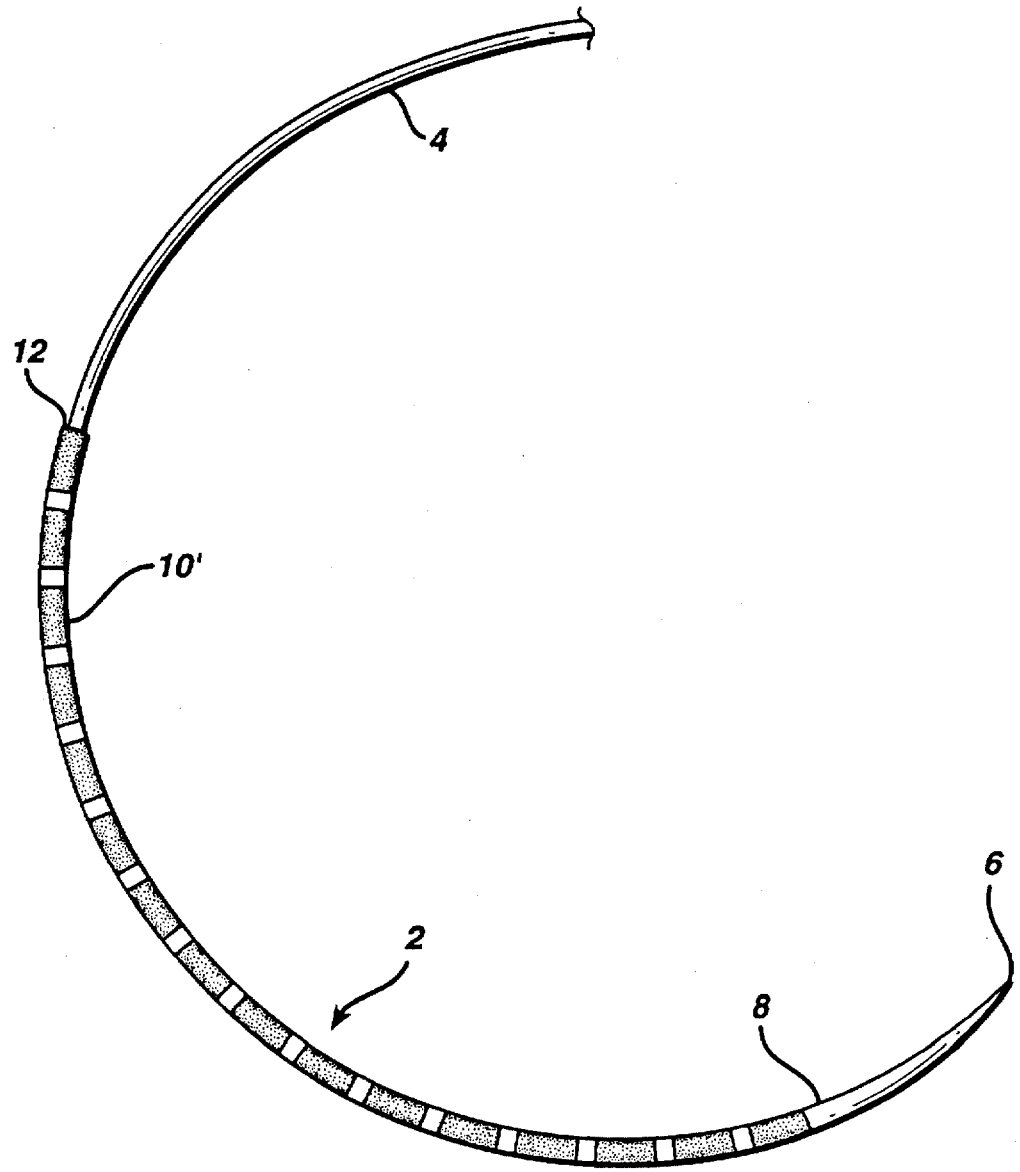
FIG. 2 a representation identical to FIG. 1 with an only zonally dulled or coloured area in ring form.

In the case of FIG. 2 the dulled or coloured area 10' is dulled or coloured in ring form. The randomly wide, dulled or coloured rings are spaced by approximately 1 to 2 mm. This spacing is sufficient to avoid any glare, but is also sufficient to make it possible to adequately detect the further contour of the needle in the operating field.

Figure 3:
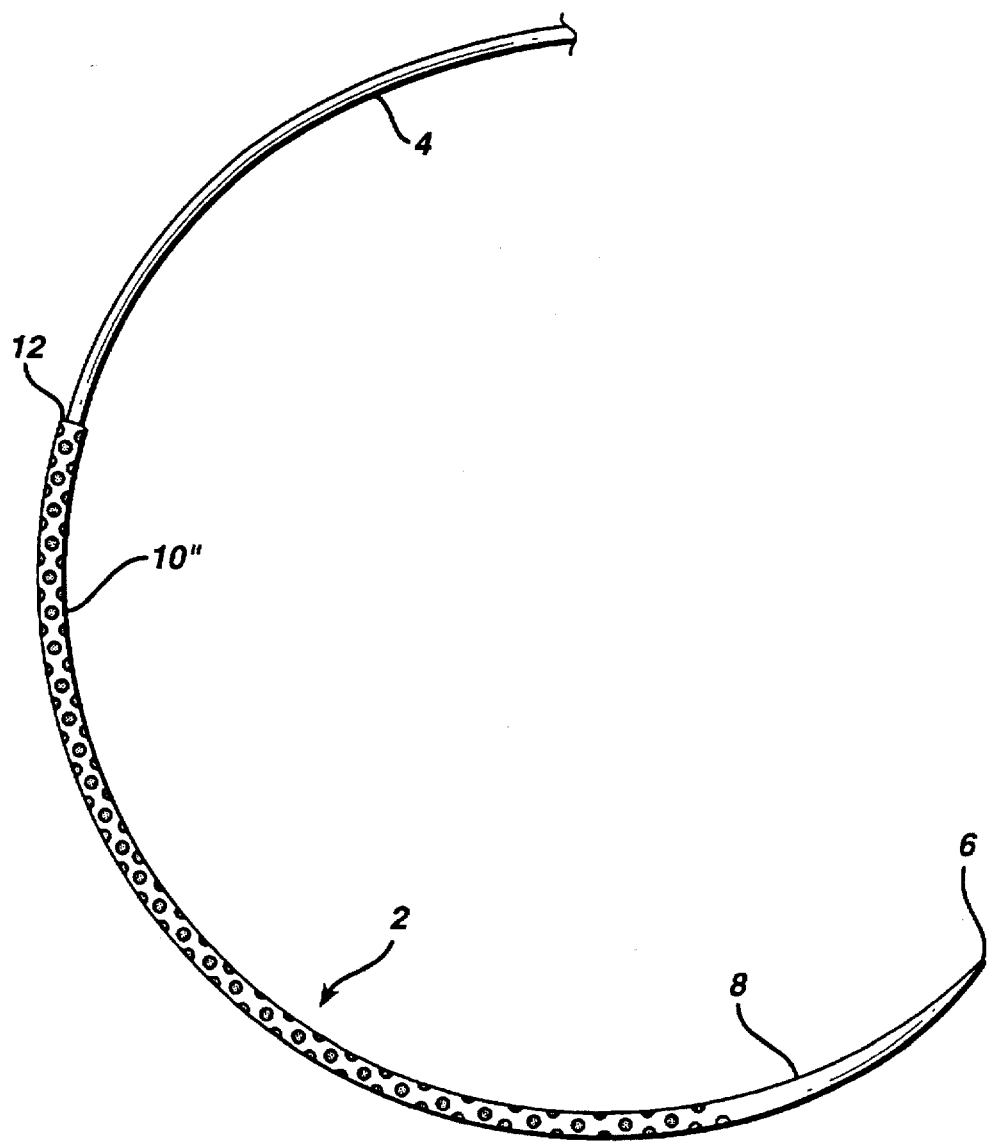
FIG. 3 a representation identical to FIG. 2 with a dulled or coloured area in speckled form.

In the needle shown in FIG. 3 the dulled or coloured area 10" is speckled and the spacings of the coloured or dulled speckles must be no greater than 1 to 2 mm.

In all the needles shown the colour of the dulled or coloured areas 8 preferably coincides with the colour of the thread 4, which leads to the further advantage that the coding colour of the thread can be detected by intuition in the case of needles in a pack.

I claim:

1. A metal, surgical needle, comprising:
    an elongated needle member, said member having a distal end, a proximal end, and an outer surface;
    a piercing tip extending from the distal end of the needle member; and,
    suture mounting means in the proximal end of the needle member,
    wherein the needle has an uninterrupted, non-reflective light-absorbing coating over the outer surface extending from the proximal end of the needle member up to about 50% of the length of needle member, and, the remaining outer surface of the needle is bar metal.

2. The needle of claim 1 wherein less than about 25% of the length of the needle extending from the proximal end has a coated outer surface and the remaining outer surface is bare metal.

3. The needle of claim 1 wherein the length of the needle having a bare outer surface as measured from the piercing tip is about 4 to about 10 mm.

4. The needle of claim 1 wherein the coated surface is discontinuous and comprises bands of coating separated by bands of uncoated outer surface.

5. The needle of claim 1 wherein the coating is discontinuous and comprises speckles of coating separated by bare surface.

6. A metal, surgical needle, comprising:

an elongated needle member, said member having a distal end, a proximal end, and outer surface;

a piercing tip extending from the distal end of the needle member; and suture mounting means in the proximal end of the needle member, wherein the needle has an uninterrupted, non-reflective, light-absorbing, dulled treatment on the outer surface extending from the proximal end of the needle member up to about 50% of the length of needle member, and, the remaining outer surface of the needle is bar metal.

7. The needle of claim 6 wherein less than about 25% of the length of the needle extending from the proximal end has a dulled treated outer surface and the remaining outer surface is bare metal.

8. The needle of claim 6 wherein the length of the needle having a bare, untreated outer surface as measured from the piercing tip is about 4 to about 10 mm.

9. The needle of claim 6 wherein the treated outer surface is discontinuous and comprises bands of treated outer surface separated by bands of untreated outer surface.

10. The needle of claim 6 wherein the treated outer surface is discontinuous and comprises speckles of treated outer surface separated by bare outer surface.

* * * * *